United States Patent
Ali et al.

(10) Patent No.: US 12,076,339 B1
(45) Date of Patent: Sep. 3, 2024

(54) **METHOD OF MAKING GOLD NANOPARTICLES CAPPED WITH *CARALLUMA sINAICA* EXTRACT AND TREATMENT METHOD USING THE SAME**

(71) Applicant: KING FAISAL UNIVERSITY, Al-Ahsa (SA)

(72) Inventors: Enas Mohamed Ali, Al Hasa (SA); Basem Mohamed Abdallah, Al Hasa (SA)

(73) Assignee: KING FAISAL UNIVERSITY, Al Hasa (SA)

( * ) Notice: Subject to any disclaimer, the term of this patent is extended or adjusted under 35 U.S.C. 154(b) by 0 days.

(21) Appl. No.: 18/518,823

(22) Filed: Nov. 24, 2023

(51) Int. Cl.
*A61K 9/51* (2006.01)
*A61K 9/14* (2006.01)
*A61K 9/16* (2006.01)
*A61K 33/242* (2019.01)

(52) U.S. Cl.
CPC ............ *A61K 33/242* (2019.01); *A61K 9/148* (2013.01); *A61K 9/1694* (2013.01)

(58) Field of Classification Search
None
See application file for complete search history.

(56) References Cited

U.S. PATENT DOCUMENTS 9,198,434 B1 * 12/2015 Alkubaisi .............. A01N 59/16
2015/0024204 A1 * 1/2015 Amanchi Bala ..... C22B 15/0089
423/604
2016/0128375 A1 * 5/2016 Isak ........................ A23L 27/60
426/321

FOREIGN PATENT DOCUMENTS

KR 20180000784 A * 1/2018

OTHER PUBLICATIONS

Alamier, Waleed M., et al. "Silver Nanoparticles' Biogenic Synthesis Using Caralluma subulata Aqueous Extract and Application for Dye Degradation and Antimicrobials Activities." Catalysts 13.9 (2023): 1290.

El-Shiekh, Riham A., et al. "Bioguided isolation of antibiofilm and antibacterial pregnane glycosides from Caralluma quadrangula: Disarming multidrug-resistant pathogens." Antibiotics 10.7 (2021): 811.

Zarei, Zahra, Damoun Razmjoue, and Javad Karimi. "Green synthesis of silver nanoparticles from Caralluma tuberculata extract and its antibacterial activity." Journal of Inorganic and Organometallic Polymers and Materials 30 (2020): 4606-4614.

Albalawi, Marzough Aziz Dager, Nour Ahmed Osman Bashir, and Amany Tawfik. "Anticancer and antifolate activities of extracts of six Saudi Arabian wild plants used in folk medicine." J. Life Sci 9 (2015): 334-340.

* cited by examiner

*Primary Examiner* — Susan T Tran
(74) *Attorney, Agent, or Firm* — Nath, Goldberg & Meyer; Joshua B. Goldberg

(57) ABSTRACT

In order to inhibit the growth of bacteria, such as methicillin-resistant *S. aureus* (MRSA), gold nanoparticles are synthesized and capped with an extract of *Caralluma sinaica*. The gold nanoparticles capped with the extract of *Caralluma sinaica* are made by adding the extract of *Caralluma sinaica* to an aqueous $HAuCl_4$ solution to reduce the $HAuCl_4$ and form a suspension of gold nanoparticles capped with the extract of *Caralluma sinaica*. An unreacted portion of the extract of *Caralluma sinaica* is removed from the suspension by centrifugation or the like, and the gold nanoparticles capped with the extract of *Caralluma sinaica* are then removed from the suspension by further centrifugation or the like. The gold nanoparticles capped with *Caralluma sinaica* extract exhibit strong antibacterial activity. To treat a MRSA infection, an effective dose of the gold nanoparticles capped with *Caralluma sinaica* extract may be administered to a patient in need thereof.

6 Claims, No Drawings

METHOD OF MAKING GOLD NANOPARTICLES CAPPED WITH *CARALLUMA sINAICA* EXTRACT AND TREATMENT METHOD USING THE SAME

BACKGROUND

Field

The disclosure of the present patent application relates to antibacterial agents, and particularly to a method of making gold nanoparticles capped with *Caralluma sinaica* extract, and further to a treatment method using the gold nanoparticles capped with *Caralluma sinaica* extract to inhibit growth of bacteria, such as methicillin-resistant *S. aureus* (MRSA).

Description of Related Art

Methicillin-resistant *Staphylococcus aureus* (MRSA) is a group of gram-positive bacteria that are genetically distinct from other strains of *Staphylococcus aureus*. MRSA is responsible for several types of infections in humans which are particularly difficult to treat. MRSA includes bacteria which has developed or acquired a multiple drug resistance to beta-lactam antibiotics. Beta-lactam antibiotics are a broad-spectrum group that include some penams, such as methicillin and oxacillin, and cephems, such as the cephalosporins.

Due to the resistance of MRSA to traditional antibiotics, alternative treatments are of great interest. Nanoparticles, both alone and used as carriers of antibacterial agents, provide a promising avenue for treatment of MRSA. Presently, metallic nanoparticles are the most commonly used type of nanoparticles in MRSA therapy and act as both antibacterial agents and drug nanocarriers. Metallic nanoparticles have the ability to eradicate microorganisms by disturbing their structure and functions. Specifically, the nanoparticles are capable of disrupting the bacterial cell wall and cell membrane when positively charged ions of the nanoparticles bind to negatively charged components. This leads to the formation of pores in the membrane, which allows cytoplasmic content to leak from the bacteria, potentially leading to cell death.

Moreover, the entry of nanoparticles into the bacterial cytoplasm induces ROS formation, which may cause DNA damage and cell death. Various metallic nanoparticles have been proposed for the targeted treatment of MRSA, including gold (Au) nanostructures, silver (Ag) nanoparticles, magnetite nanoparticles, and zinc (Zn) nanoparticles.

Gold nanoparticles have received a great deal of interest in recent years for the treatment of MRSA. Although the gold nanoparticles are somewhat effective on their own, using the gold nanoparticles as both treatment agents and nanocarriers for additional antibacterial agents is generally viewed as a highly promising treatment for most types of MRSA infection. Since functionalizing or capping the gold nanoparticles with traditional antibiotics would not be effective against MRSA, alternative agents, such as plant phytochemicals with antibacterial properties, are of interest. Thus, a method of making gold nanoparticles capped with *Caralluma sinaica* extract and a treatment method using the same solving the aforementioned problems are desired.

SUMMARY

In order to inhibit the growth of bacteria, such as methicillin-resistant *S. aureus* (MRSA), as a non-limiting example, gold nanoparticles are synthesized and capped with an extract of *Caralluma sinaica*, a perennial desert succulent plant. The gold nanoparticles capped with the extract of *Caralluma sinaica* are made by adding the extract of *Caralluma sinaica* to an aqueous $HAuCl_4$ solution to reduce the $HAuCl_4$ and form a suspension of gold nanoparticles capped with the extract of *Caralluma sinaica*. The extract of *Caralluma sinaica* acts as a reducing and stabilizing agent while also functionalizing the surfaces of the gold nanoparticles to cap the surfaces with the extract of *Caralluma sinaica*.

The unreacted portion of the extract of *Caralluma sinaica* is removed from the suspension by centrifugation or the like, and the gold nanoparticles capped with the extract of *Caralluma sinaica* are then removed from the suspension by further centrifugation or the like.

In order to make the extract of *Caralluma sinaica*, *Caralluma sinaica* stem is air dried and pulverized to form powdered *Caralluma sinaica*. The powdered *Caralluma sinaica* is mixed into water to form a mixture, and the mixture is heated under reflux to form a decoction (i.e., a liquor). The decoction is then concentrated to form the extract of *Caralluma sinaica*. As a non-limiting example, the decoction may be concentrated in a rotary vacuum evaporator. Prior to concentration in the rotary vacuum evaporator, the decoction may be centrifuged and filtered.

The gold nanoparticles capped with *Caralluma sinaica* extract exhibit strong antibacterial activity. In order to treat a methicillin-resistant *S. aureus* (MRSA) infection, an effective dose of the gold nanoparticles capped with *Caralluma sinaica* extract may be administered to a patient in need thereof.

These and other features of the present subject matter will become readily apparent upon further review of the following specification.

DETAILED DESCRIPTION

In order to inhibit the growth of bacteria, such as methicillin-resistant *S. aureus* (MRSA), as a non-limiting example, gold nanoparticles are synthesized and capped with an extract of *Caralluma sinaica*, a perennial desert succulent plant. The gold nanoparticles capped with the extract of *Caralluma sinaica* are made by adding the extract of *Caralluma sinaica* to an aqueous $HAuCl_4$ solution to reduce the $HAuCl_4$ and form a suspension of gold nanoparticles capped with the extract of *Caralluma sinaica*. The extract of *Caralluma sinaica* acts as a reducing and stabilizing agent while also functionalizing the surfaces of the gold nanoparticles to cap the surfaces with the extract of *Caralluma sinaica*.

The unreacted portion of the extract of *Caralluma sinaica* is removed from the suspension by centrifugation or the like, and the gold nanoparticles capped with the extract of *Caralluma sinaica* are then removed from the suspension by further centrifugation or the like.

In order to make the extract of *Caralluma sinaica*, *Caralluma sinaica* stem is air dried and pulverized to form powdered *Caralluma sinaica*. The powdered *Caralluma sinaica* is mixed into water to form a mixture, and the mixture is heated under reflux to form a decoction (i.e., a liquor). The decoction is then concentrated to form the extract of *Caralluma sinaica*. As a non-limiting example, the decoction may be concentrated in a rotary vacuum evaporator. Prior to concentration in the rotary vacuum evaporator, the decoction may be centrifuged and filtered.

The gold nanoparticles capped with *Caralluma sinaica* extract exhibit strong antibacterial activity. In order to treat a methicillin-resistant *S. aureus* (MRSA) infection, an effective dose of the gold nanoparticles capped with *Caralluma sinaica* extract may be administered to a patient in need thereof.

Example 1

10 mL of *Caralluma sinaica* extract was added to 50 mL of 1 mM aqueous $HAuCl_4$ solution. A change of color from pale yellow to vivid ruby-red demonstrated the reduction of $HAuCl_4$ and the formation of gold nanoparticles. The suspension was centrifuged at 4000 rpm for 12 minutes to remove the unreacted plant extract. The biosynthesized nanoparticles were collected by centrifugation at 15,000 rpm for 25 minutes and purified by washing with sterile distilled water to obtain the nanoparticles in pellet form. The purified gold nanoparticles capped with *Caralluma sinaica* extract were then suspended in distilled water for further study.

Example 2

The stem of *Caralluma sinaica* was air dried and then pulverized. An aqueous extract was prepared by adding 2 L of distilled water to 200 g of the *Caralluma sinaica* stem powder. This mixture was heated under reflux at 65° C. for one hour in a round-bottom flask. The boiled decoction was centrifuged, filtered, and concentrated in a rotary vacuum evaporator at 45° C. The extracted material was stored at −20° C. until used as the *Caralluma sinaica* extract in the method described in Example 1 above.

It is to be understood that the method of making gold nanoparticles capped with *Caralluma sinaica* extract and the treatment method using the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method of treating methicillin-resistant *S. aureus* infection, comprising administering to a patient in need thereof an effective dose of gold nanoparticles capped with *Caralluma sinaica* extract, the gold nanoparticles capped with *Caralluma sinaica* extract made according to a method comprising the steps of:
   adding an extract of *Caralluma sinaica* to an aqueous $HAuCl_4$ solution to reduce the $HAuCl_4$ and form a suspension of gold nanoparticles capped with the extract of *Caralluma sinaica*;
   removing an unreacted portion of the extract of *Caralluma sinaica* from the suspension; and
   collecting the gold nanoparticles capped with the extract of *Caralluma sinaica* from the suspension.

2. The method of treating methicillin-resistant *S. aureus* infection as recited in claim 1, wherein the step of removing the unreacted portion of the extract of *Caralluma sinaica* from the suspension comprises centrifuging the suspension.

3. The method of treating methicillin-resistant *S. aureus* infection as recited in claim 2, wherein the step of collecting the gold nanoparticles capped with the extract of *Caralluma sinaica* from the suspension comprises further centrifuging the suspension.

4. The method of treating methicillin-resistant *S. aureus* infection as recited in claim 1, further comprising the steps of:
   air drying and pulverizing a stem of *Caralluma sinaica* to form powdered *Caralluma sinaica*;
   mixing the powdered *Caralluma sinaica* into water to form a mixture;
   heating the mixture under reflux to form a decoction; and
   concentrating the decoction to form the extract of *Caralluma sinaica*.

5. The method of treating methicillin-resistant *S. aureus* infection as recited in claim 4, wherein the step of concentrating the decoction is performed in a rotary vacuum evaporator.

6. The method of treating methicillin-resistant *S. aureus* infection as recited in claim 5, further comprising centrifuging and filtering the decoction prior to concentration thereof in the rotary vacuum evaporator.

* * * * *